United States Patent
Judisch et al.

(10) Patent No.: US 11,253,690 B2
(45) Date of Patent: Feb. 22, 2022

(54) CIRCULATORY ASSIST DEVICE

(71) Applicant: Boston Scientific Scimed, Inc., Maple Grove, MN (US)

(72) Inventors: August Judisch, Minneapolis, MN (US); Eric Musselman, Durham, NC (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 186 days.

(21) Appl. No.: 16/351,258

(22) Filed: Mar. 12, 2019

(65) Prior Publication Data

US 2019/0282746 A1    Sep. 19, 2019

Related U.S. Application Data

(60) Provisional application No. 62/642,103, filed on Mar. 13, 2018.

(51) Int. Cl.
*A61M 1/12*        (2006.01)
*A61M 60/135*    (2021.01)
(Continued)

(52) U.S. Cl.
CPC .......... *A61M 60/135* (2021.01); *A61M 39/22* (2013.01); *A61M 60/148* (2021.01);
(Continued)

(58) Field of Classification Search
CPC .. A61M 1/125; A61M 1/1053; A61M 1/1008; A61M 1/1087; A61M 1/122;
(Continued)

(56) References Cited

U.S. PATENT DOCUMENTS

2016/0144091 A1*   5/2016   Breedon ............. A61M 60/148
                                                        623/3.29

FOREIGN PATENT DOCUMENTS

| WO | 03/81762 A1 | 10/2003 |
| WO | 2004/031582 A1 | 4/2004 |
| WO | 2014/199167 A1 | 12/2014 |

OTHER PUBLICATIONS

International Search Report and Written Opinion received for PCT Patent Application No. PCT/US2019/021902, dated Jun. 14, 2019, 9 pages.

* cited by examiner

*Primary Examiner* — Rex R Holmes
(74) *Attorney, Agent, or Firm* — Faegre Drinker Biddle & Reath LLP

(57) ABSTRACT

An example medical device is disclosed. The example medical device includes a tubular scaffold having an inner surface and an outer surface. The medical device also includes a flexible inner member extending along at least a portion of the inner surface of the scaffold. Further, the medical device includes an activation assembly positioned along a portion of the inner member, the activation assembly including a conductive member having a first end region and a second end region, wherein a portion of the first end region is coupled to an activation element, and wherein the second end region is coupled to a power source. Additionally, the power source is configured to deliver an electrical stimulus to the activation element which shifts the inner member between a first configuration and a second expanded configuration.

11 Claims, 16 Drawing Sheets

(51) Int. Cl.
    *A61M 39/22*         (2006.01)
    *A61M 60/40*         (2021.01)
    *A61M 60/148*       (2021.01)
    *A61M 60/284*       (2021.01)
    *A61M 60/857*       (2021.01)
    *A61M 60/871*       (2021.01)
    *A61M 60/892*       (2021.01)

(52) U.S. Cl.
    CPC .......... *A61M 60/284* (2021.01); *A61M 60/40* (2021.01); *A61M 60/857* (2021.01); *A61M 60/871* (2021.01); *A61M 60/892* (2021.01); *A61M 2039/226* (2013.01); *A61M 2205/0283* (2013.01); *A61M 2205/3334* (2013.01)

(58) Field of Classification Search
    CPC .... A61M 1/1041; A61M 1/127; A61M 39/22; A61M 2039/226; A61M 2205/0283; A61M 2205/3334
    See application file for complete search history.

US 11,253,690 B2

CIRCULATORY ASSIST DEVICE

CROSS-REFERENCE TO RELATED APPLICATION

This application claims priority to Provisional Application No. 62/642,103, filed Mar. 13, 2018, which is herein incorporated by reference in its entirety.

TECHNICAL FIELD

The present disclosure pertains to medical devices, and methods for manufacturing medical devices. More particularly, the present disclosure pertains to medical devices including a tubular scaffold having an inner pumping member, and methods for manufacturing and using such medical devices.

BACKGROUND

A wide variety of medical devices have been developed for medical use including, for example, medical devices utilized to assist the heart in pumping blood throughout the circulatory system. These medical devices are manufactured, packaged, and used according to any one of a variety of different methods. Of the known medical devices and methods, each has certain advantages and disadvantages. There is an ongoing need to provide alternative medical devices as well as alternative methods for manufacturing, packaging, and using the medical devices.

BRIEF SUMMARY

This disclosure provides design, material, manufacturing method, and use alternatives for medical devices. An example medical device includes a tubular scaffold, the scaffold including an inner surface and an outer surface. The medical device also includes a flexible inner member extending along at least a portion of the inner surface of the scaffold. Further, the medical device includes an activation assembly positioned along a portion of the inner member, the activation assembly including a conductive member having a first end region and a second end region, wherein a portion of the first end region is coupled to an activation element, and wherein the second end region is coupled to a power source. Additionally, the power source is configured to deliver an electrical stimulus to the activation element and electrical stimulation of the activation element shifts the inner member between a first configuration and a second expanded configuration.

Alternatively or additionally to any of the embodiments above, the inner member includes an electroactive polymer.

Alternatively or additionally to any of the embodiments above, wherein the activation element includes an electrode positioned within at least a portion of a wall of the inner member.

Alternatively or additionally to any of the embodiments above, wherein the activation element includes one or more additional electrodes positioned within at least a portion of a wall of the inner member.

Alternatively or additionally to any of the embodiments above, wherein the electrodes include a first set of electrodes, and wherein each of the first set of electrodes is at the same axial position along a longitudinal axis of the inner member.

Alternatively or additionally to any of the embodiments above, wherein each electrode of the first set of electrodes is circumferentially spaced around the longitudinal axis of the inner member.

Alternatively or additionally to any of the embodiments above, wherein the electrodes further include a second set of electrodes, and wherein the second set of electrodes is spaced away from the first set of electrodes along the longitudinal axis of the inner member.

Alternatively or additionally to any of the embodiments above, wherein each of the second set of electrodes is at the same axial position along a longitudinal axis of the inner member.

Alternatively or additionally to any of the embodiments above, further comprising a valve, wherein the valve is formed from at least a portion of the inner member.

Alternatively or additionally to any of the embodiments above, wherein the inner member includes a first attachment region, a second attachment region and a medial region extending between the first and second attachment regions, an wherein the medial region is free from attachment to the inner surface of the scaffold.

Alternatively or additionally to any of the embodiments above, wherein shifting the inner member from the first configuration to the second expanded configuration is configured to draw blood into a lumen of the inner member, and wherein shifting the inner member from the second expanded configuration to the first configuration is configured to pump blood out of the lumen of the inner member.

Alternatively or additionally to any of the embodiments above, wherein the activation element includes a plurality of artificial muscle strands positioned along an outer surface of the inner member.

Alternatively or additionally to any of the embodiments above, wherein electrical stimulation of the artificial muscle strands shifts the inner member between the first configuration and the second expanded configuration.

Alternatively or additionally to any of the embodiments above, wherein electrical stimulation of the artificial muscle strands increases the outer diameter of one or more of the muscle strands.

Another example medical device includes:
a tubular stent, the stent including an inner surface and an outer surface;
an inner member extending along at least a portion of the inner surface of the stent, the inner member including an inner surface, an outer surface and a wall extending therebetween;
a first set of electrodes positioned at least partially within the wall of the inner member, wherein the set of electrodes is spaced circumferentially around a longitudinal axis of the inner member; and
a wire having a first end region and a second end region, wherein a portion of the first end region couples each of the plurality of electrodes to one another, and wherein the second end region is coupled to a power source;
wherein the power source is configured to deliver an electrical stimulus to the at least one of the plurality of electrodes, and wherein electrical stimulation of the at least one electrode shifts the inner member between a first configuration and a second expanded configuration.

Alternatively or additionally to any of the embodiments above, wherein the inner member includes an electroactive polymer.

Alternatively or additionally to any of the embodiments above, further comprising a second set of electrodes, and wherein the second set of electrodes is spaced away from the first set of electrodes along the longitudinal axis of the inner member.

Alternatively or additionally to any of the embodiments above, wherein each of the first set of electrodes is at the same axial position along a longitudinal axis of the inner member and wherein each of the second set of electrodes is at the same axial position along the longitudinal axis of the inner member.

Alternatively or additionally to any of the embodiments above, wherein the wire couples the first set of electrodes to the second set of electrodes.

Another example medical stent for pumping blood includes:

a tubular scaffold, the scaffold including an inner surface and a lumen extending therein;

a flexible sleeve extending along at least a portion of the inner surface of the scaffold, wherein at least a portion of the sleeve includes an electroactive polymer; and a conductive member having a first end region and a second end region, wherein a portion of the first end region is coupled to the electroactive polymer and wherein the second end region is coupled to a power source;

wherein the power source is configured to deliver an electrical stimulus to the electroactive polymer;

wherein electrical stimulation of the activation member shifts the inner member between a narrowed configuration and an expanded configuration.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
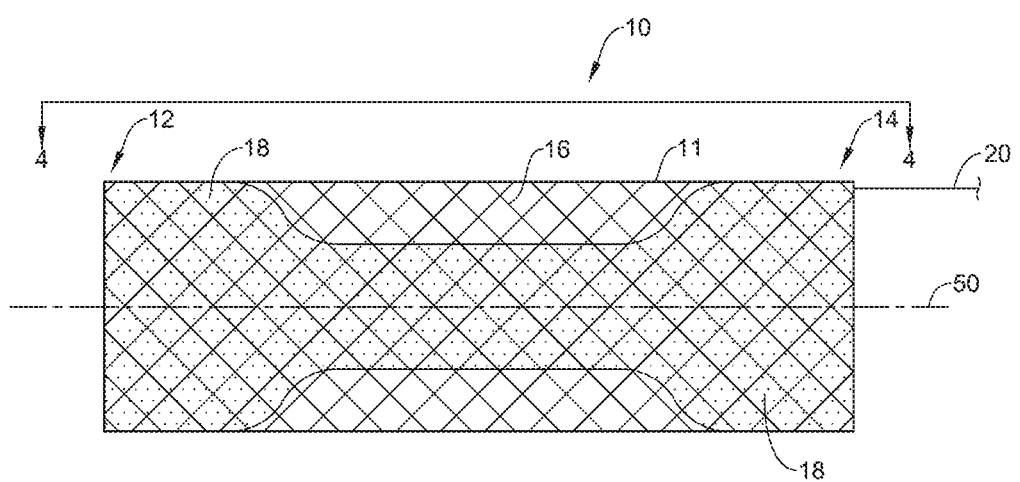
FIG. 1 is an example medical device including a tubular scaffold and inner member.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the disclosure.

FIG. 1 shows an example medical device 10. The medical device 10 may have a first end 12, a second end 14 and a lumen extending therein having a central longitudinal axis 50. Additionally, the medical device 10 may include one or more stent strut members 16 forming a tubular scaffold 11. The tubular scaffold 11 may be referred to as a stent herein. The stent strut members 16 may extend helically, longitudinally, circumferentially, or otherwise along the medical device 10. While FIG. 1 shows the stent strut members 16 extending along the entire length of the medical device 10, other examples are contemplated in which the stent strut members 16 may extend only along a portion of the medical device 10.

In some instances, the stent 11 may be a self-expanding stent or the stent 11 may be a balloon expandable stent. The self-expanding stent examples may include stents having one or more struts 16 combined to form a rigid and/or semi-rigid stent structure. For example, the stent struts 16 may be wires or filaments which are braided, wrapped, intertwined, interwoven, weaved, knitted, looped (e.g., bobbinet-style) or the like to form the stent structure. For example, while the example stents disclosed herein may resemble a braided stent, this is not intended to limit the possible stent configurations. Rather, the stents depicted in the figures may be stents that are knitted, braided, wrapped, intertwined, interwoven, weaved, looped (e.g., bobbinet-style) or the like to form the stent structure. Alternatively, the stent 11 may be a monolithic structure formed from a cylindrical tubular member, such as a single, cylindrical tubular laser-cut Nitinol tubular member, in which the remaining portions of the tubular member form the stent struts 16. Openings or interstices through the wall of the stent 11 may be defined between adjacent stent struts 16.

The stent 11 in the examples disclosed herein may be constructed from a variety of materials. For example, the stent 11 (e.g., self-expanding or balloon expandable) may be constructed from a metal (e.g., Nitinol, Elgiloy, etc.). In other instances, the stent 11 may be constructed from a polymeric material (e.g., PET). In yet other instances, the stent 11 may be constructed from a combination of metallic and polymeric materials. Additionally, the stent 11 may include a bioabsorbable and/or biodegradable material.

In some instances, the example medical device 10 may include one or more members positioned on and/or adjacent to the inner surface of the stent 11 of the medical device 10. For example, FIG. 1 shows the example medical device 10 including an inner member 18 (depicted as a dotted pattern in FIG. 1) disposed along a portion of the inner surface (e.g., within the lumen) of the stent 11. In some instances, the inner member 18 may be an elastomeric or non-elastomeric material. For example, the inner member 18 may be a polymeric material, an electroactive polymer (e.g., polypyrrole), silicone, polyurethane, or combinations thereof.

For purposes of the discussion herein, the inner member 18 may be interchangeably referred to as an inner sleeve, tube, liner, or the like. The inner member 18 may extend circumferentially around the lumen of the stent 11. In other words, it can be appreciated that the inner member 18 may be defined as an annular layer that extends continuously around the lumen of the stent 11. Further, the inner member 18 may extend continuously (e.g., uninterrupted) around the lumen of the stent 11, from the first end 12 to the second end 14.

In some examples, the inner member 18 may touch and/or form an interface region within the spaces (e.g., openings, cells, interstices) in the wall of the stent 11 of the medical device 10. Further, the inner member 18 may additionally extend between adjacent struts 16, thereby filling any space between adjacent strut members 16 of the stent 11. The stent 11 may include areas in which one or more struts 16 are surrounded, encased and/or covered by the inner member 18. For example, some portions of the stent 11 may include struts 16 which are encapsulated by the inner member 18.

As will be described in greater detail below, FIG. 1 further illustrates that the medical device 10 may include a conductive member 20 coupled thereto. The conductive member 20 may be coupled to one or more "activation elements" of the medical device 10 which are designed to respond to an electrical stimulus. In some examples, the conductive member 20 may include a metal wire or similar conductive material.

Figure 2:
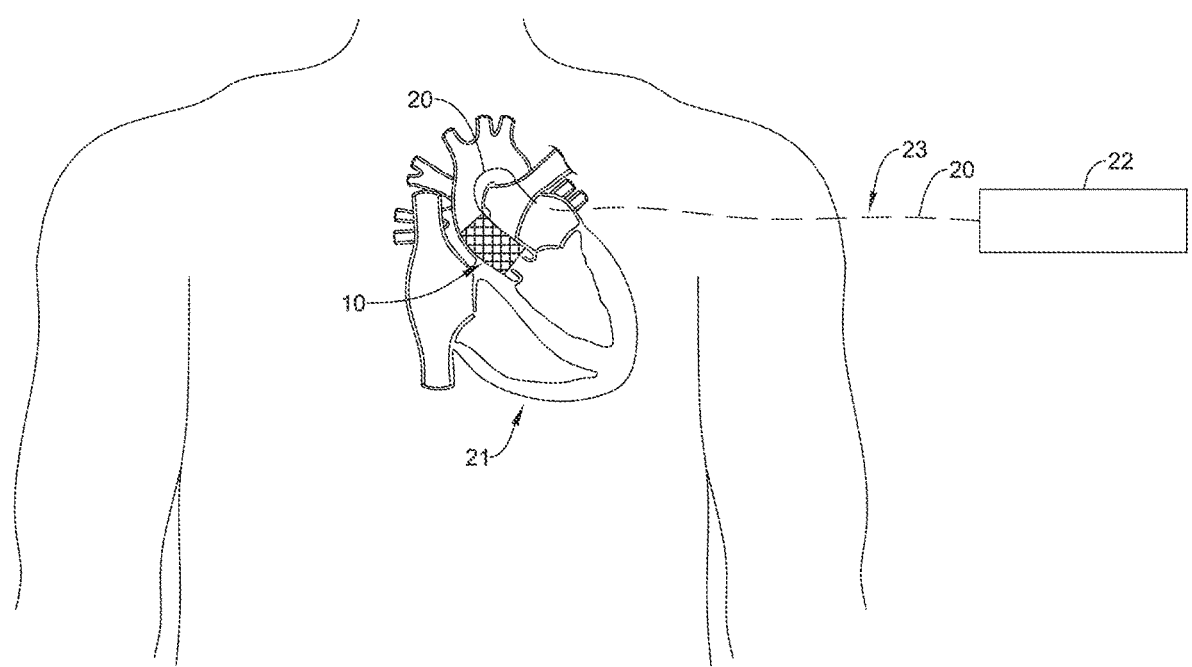
FIG. 2 illustrates the medical device of FIG. 1 positioned within the body.

FIG. 2 illustrates the medical device 10 positioned within the heart 21 of a patient. Additionally, FIG. 2 illustrates the conductive member 20 including a first end coupled to the medical device 10 and a second end coupled to a power source 22. In the example shown in FIG. 2, the power source 22 is positioned outside the patient's body. It can be appreciated that dashed portion 23 of the conductive member 20 represents that the conductive member 20 may extend through and exit the body through a variety of configurations. For example, the conductive member 20 may extend through one or more body lumens and attach to a power source positioned adjacent the waist of a patient.

The above discussion describing examples in which the power source 22 is positioned outside a patient's body is not intended to be limiting. Rather, it is contemplated that in some examples the power source 22 may be positioned inside a patient. For example, in some instances the conductive member 20 may be coupled to an internal pacemaker (e.g., a low-voltage pacemaker or similar internal power source). In other words, the medical device 10, the conductive member 20 and the power source 22 may be contained within a patient's body.

Figure 3:
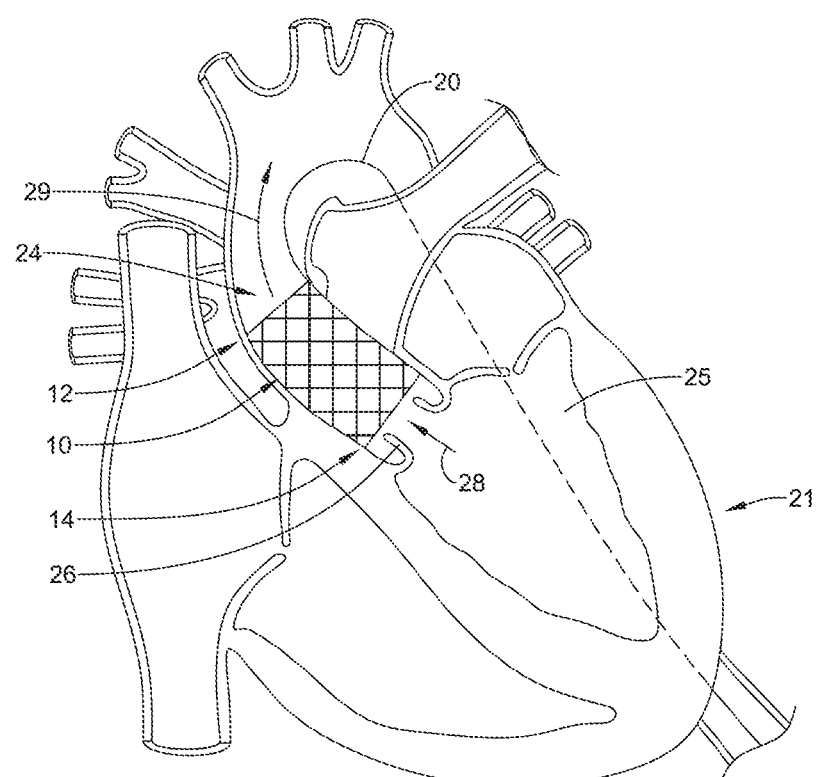
FIG. 3 illustrates the medical device of FIG. 1 positioned in the aorta.

FIG. 3 illustrates the medical device 10 positioned within the ascending aorta 24 of the heart 21. As discussed above, the medical device 10 may be designed to assist the heart in providing supplemental pumping action for blood exiting the left ventricle 25 via the aortic valve 26. As shown in FIG. 2, placement of the medical device 10 adjacent to the aortic valve 26 may be beneficial as the blood (depicted by arrow 28) exiting the left ventricle 25 may enter the second end 14 of the medical device 10 whereby the medical device 10 pumps the blood such that it exits the first end 12 of the medical device 10 (the blood exiting the medical device 10 is depicted by arrow 29 in FIG. 3) with additional force than was provided solely by the left ventricle 25. It can be appreciated that the additional pumping action of the medical device 10 may assist the heart 21 in circulating blood throughout the body. It is noted that while the above discussion describes the benefits of utilizing the medical device 10 in the heart, it is contemplated that the medical device 10 may be utilized in other portions (e.g., other body lumens) of the body.

Figure 4:
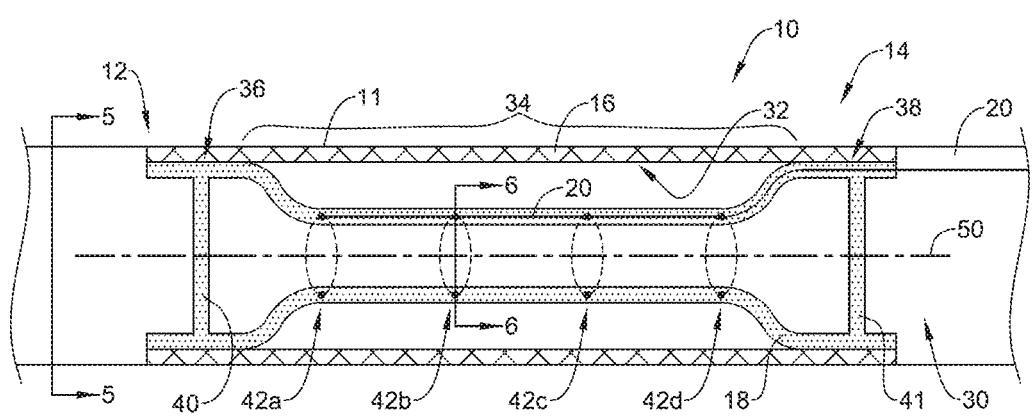
FIG. 4 is a cross-sectional view taken along line 4-4 of FIG. 1.

FIG. 4 illustrates a cross-sectional view of example medical device 10 along line 4-4 of FIG. 1. FIG. 4 shows the medical device 10 positioned inside an example body lumen 30 (e.g., the ascending aorta of the heart). FIG. 4 illustrates the inner member 18 extending along all or a portion of the inner surface 32 of the stent 11. FIG. 4 illustrates that the inner member 18 may be fixedly attached along the inner surface of the first end region 12 and the second end region 14. In other words, FIG. 4 illustrates that the inner member 18 may be attached (e.g., affixed, secured, etc.) to the inner surface 32 of the strut members 16 positioned along the first end region 12 and the second end region 14 of the stent 11.

Additionally, FIG. 4 illustrates that, in some examples, a portion of the inner member 18 may be spaced away from (i.e., spaced radially inward of) the inner surface 32 of the stent 11, providing a gap or space therebetween. In particular, FIG. 4 illustrates that the portion of the inner member 18 extending along a medial region 34 of the stent 11 may be free from attachment and spaced radially inward from the inner surface 32 of the stent 11 of medical device 10. For example, FIG. 4 shows that layer 18 may be attached (e.g., circumferentially) along a first attachment region 36 and a second attachment region 38, with the length of layer 18 between attachment regions 36/38 remaining unattached (i.e., not directly attached) to the stent 11 of the medical device 10. FIG. 4 shows that the inner member 18 may be unattached to the inner surface 32 of the stent 11 (e.g., the struts 16) of the medical device 10 along a portion of medical device 10 between the first attachment point 36 and the second attachment point 38. In other words, the inner member 18 may be unattached and thereby extend radially inward from the inner surface 32 of the stent 11 (i.e., struts 16) along the medial portion 34 of medical device 10. However, the above discussion is not intended to be limiting. Rather, it is contemplated that, in some examples, the inner member 18 may be attached to the inner surface 32 of the stent 11 along its entire length.

FIG. 4 further illustrates that that the medical device 10 may include a first valve member 40 and/or a second valve member 41. As will be discussed in greater detail below, the valve 40 and/or the valve 41 may be formed as a portion of the inner member 18. In other words, the valve 40 and/or the valve 41 may be unitary or monolithic structures formed in conjunction with constructing the inner member 18 on the stent 11. For example, FIG. 4 illustrates that the valve 40 and/or the valve 41 may be inwardly extending portions of the inner member 18 extending radially inward of the stent 11 along the first end region 12. In other words, the valve 40 and/or the valve 41 may be defined as a unitary or monolithic portion of the inner member 18 that extends radially inward from an inner surface of the stent 11 toward the central longitudinal axis 50 of the medical device 10. Additionally, it is contemplated that any of the example medical devices disclosed herein may include more or less than two valve members. For example, the medical devices may include 1, 2, 3, 4, 5, 6, 7, 8, or more valve members.

Further, in some examples, the valve 40 and/or the valve 41 may be defined as a monolithic portion of the inner member 18 that extends circumferentially within the lumen of the inner member 18. In other words, it can be appreciated that the valve 40 and/or the valve 41 may be defined as an annular member that extends continuously around the lumen of the inner member 18 positioned radially inward of the stent 11. Further, the valve 40 and/or the valve 41 may be defined as an uninterrupted extension of the inner member 18 projecting toward central longitudinal axis 50, forming an annular disk of polymeric material extending radially inward of the stent 11.

Additionally, in some examples the medical device 10 may include one or more activation elements 42*a*, 42*b*, 42*c*, 42*d* disposed along the inner member 18. As will be discussed in greater detail below, the activation elements may include conductive elements such as electrodes. Further, the activation elements may include a plurality of individual electrodes which are grouped together in one or more "sets" of electrodes. For example, FIG. 4 illustrates that the medical device 10 may include four sets of activation elements 42*a*-42*d* disposed along the inner member 18. While the example medical device 10 shown in FIG. 4 illustrates four sets of electrodes 42*a*-42*d*, this is not intended to be limiting. Rather, it can be appreciated that the medical device 10 may include more or less than four sets of electrodes disposed along the inner member 18. For example, the medical device 10 may include 1, 2, 3, 4, 5, 6, 7, 8, 9, 10 or more sets of electrodes disposed along the inner member 18.

It can be appreciated that the electrodes defining each of the sets of electrodes 42*a*-42*d* may located at the same axial position along the longitudinal axis 50. In other words, as depicted by the circular, dashed lines of FIG. 4, each of the electrodes which defines an individual set of electrodes 42*a*-42*d* may be at the same axial position as one another along the longitudinal axis 50 of the medical device 10. FIG. 4 further illustrates that each of the four sets of electrode elements 42*a*-42*d* may be spaced away from one another along the longitudinal axis 50 of the medical device 10. Additionally, FIG. 4 illustrates that the conductive member 20 may be coupled to at least one electrode from each of the sets of electrodes 42*a*-42*d*. As shown in FIG. 4, the conductive member 20 may span between and connect each of the sets of electrodes 42*a*-42*d* to one another. It can be appreciated that the having the conductive member 20 connect each of the sets of electrodes 42*a*-42*d* with one another may permit each of the sets of electrodes 42*a*-42*d* to receive a conductive signal at substantially the same time. Additionally, in other examples it can be appreciated that the having the conductive member 20 connect each of the sets of electrodes 42*a*-42*d* with one another may permit each of the sets of electrodes 42*a*-42*d* to receive a conductive signal in sequence with one another.

Figure 5:
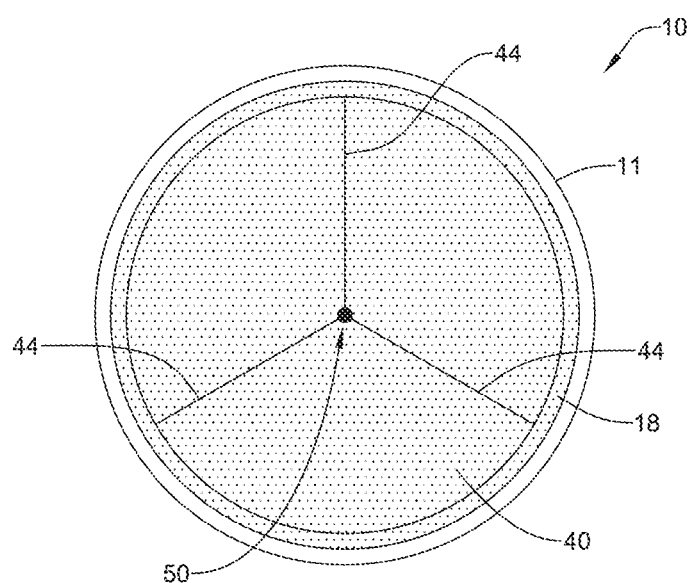
FIG. 5 is an end view taken along line 5-5 of FIG. 4.

FIG. 5 is an end view of the medical device 10 taken along line 5-5 of FIG. 4. In particular, FIG. 5 illustrates the valve member 40 extending radially inward from the inner member 18 as described above. Further, FIG. 5 shows the inner member 18 extending circumferentially around the lumen of the stent 11 of the medical device 10. FIG. 5 further illustrates that the valve 40 may include a plurality of slits 44 that extend from the inner member 18 to the central region of the valve 40 (it can be appreciated that the central region of the valve 40 may correspond to the longitudinal axis 50 of the medical device 10). As will be described in greater detail below, it can be appreciated that the plurality of slits 44 may permit the valve 40 to open and close as blood is pumped through the medical device 10. As will be described in greater detail below, the valve 40 may be a one-way valve, whereby the slits 44 permit blood to flow in one direction (e.g., from the left ventricle to the aorta) while preventing blood to flow the in opposite direction (e.g., from the aorta back in to the left ventricle). It can be appreciated that the features described above with respect to the valve 40 may also apply to the valve 41 or any other valve disposed along the medical device 10.

Figure 6:
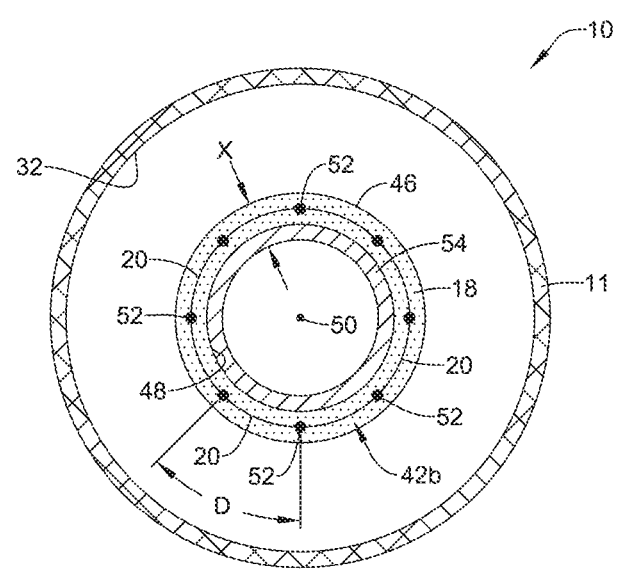
FIG. 6 illustrates an example medical device positioned in a body lumen.

FIG. 6 is a cross-sectional view taken along line 6-6 of the medical device 10. In particular, FIG. 6 illustrates a cross-section of the inner member 18 taken directly through the set of activation members 42*b* (discussed above with respect to FIG. 4). Further, FIG. 6 illustrates that the inner member 18 is spaced radially inward from the inner surface 32 of the stent 11

Additionally, FIG. 6 shows that inner member 18 may include a wall thickness "X" defined as width of the inner wall between the inner surface 48 and outer surface 46 of the inner member 18. FIG. 6 further illustrates a plurality of electrode elements 52 positioned within the wall of the inner member 18. For example, FIG. 6 shows eight electrodes 52 positioned circumferentially around the longitudinal axis 50 of the medical device 10. However, while FIG. 6 shows eight electrodes 52 positioned around the longitudinal axis 50 of the medical device 10, it is contemplated that more or less than eight electrodes 52 may be utilized to form any of the electrode sets described herein. For example, the electrode set 42*b* (along with any of the other electrode sets described above with respect to medical device 10) may include 1, 2, 3, 4, 5, 6, 7, 8, 9, 10, 15 or more electrodes disposed along the inner member 18.

FIG. 6 further shows that one or more of the electrodes 52 may be positioned radially outward of the inner surface 48 of the inner member 18. Further, each of the one or more electrodes 52 may be positioned radially inward of the outer surface 46 of the inner member 18. In other words, each of the electrodes 52 may be embedded (e.g., encased, surrounded, etc.) within the wall thickness "X" of the inner member 18. Additionally, FIG. 6 illustrates that each of the electrodes 52 may be circumferentially spaced apart from one another around the longitudinal axis 50 of the medical device 10. For example, FIG. 6 shows each of the electrodes 52 may be spaced apart from one another a distance depicted as "D" in FIG. 6. In some instances, the electrodes 52 may be spaced substantially equidistant from one another. In other words, the spacing "D" may be substantially equivalent between individual adjacent electrodes 52. However, it is further contemplated that the electrodes 52 may be spaced at variable distances around the longitudinal axis 50 of the medical device 10. It should be appreciated that the above discussed regarding the electrodes 52 of the electrode set 42b may apply to any of the electrode sets described herein.

Additionally, FIG. 6 illustrates the conductive member 20 extending between and connecting each of the electrodes 52 to one another. In other words, it can be appreciated that in some examples the conductive member 20 may not only connect each set of electrodes together (as discussed above with respect to FIG. 4), but may also connect each of the electrodes 52 within each set of electrodes to one another. It can be further appreciated that the conductive member 20 may deliver an electrical stimulus to each of the electrodes 52 within the electrode set 42b (or any other electrode set described herein).

Additionally, it is contemplated that in some examples contemplated herein, a liner 54 may be disposed along the inner surface 48 of the inner member 18. It is further contemplated that the liner 54 may extend along the length of the inner member 18. In other examples, the liner 54 may extend along only a portion of the length of the inner member 18. Further, it is contemplated that the liner 54 may include one or more coatings, such as a biocompatible material (e.g., silicone), an anti-coagulant, a lubricious coating, a hydrophilic coating, a hydrophobic coating, or other suitable coatings, and the like, or may include a lubricant disposed thereon.

As discussed above, the medical device 10 may be utilized to assist the heart in pumping blood through the circulatory system of the body. It can be appreciated that in order for the medical device 10 to sufficiently perform a pumping action, one or more components of the medical device 10 may need to radially contract or expand to squeeze blood out of the medical device 10 and into the circulatory system of the body.

Figure 7:
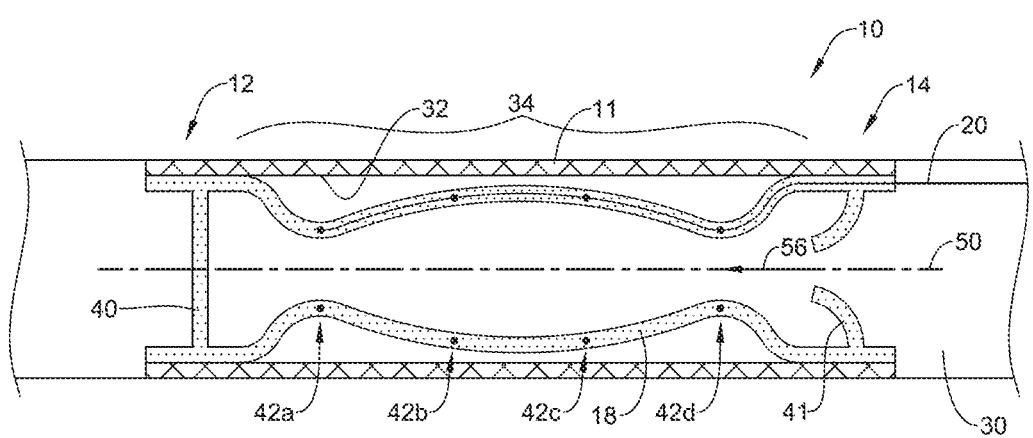
FIG. 7 illustrates the example medical device of FIG. 6 positioned in a body lumen.
Figure 8:
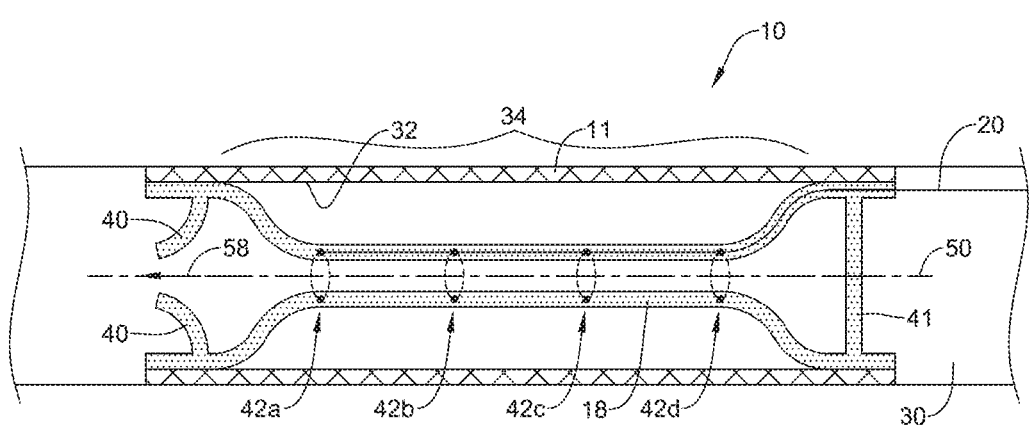
FIG. 8 illustrates the example medical device of FIG. 6 positioned in a body lumen.

FIGS. 7-8 illustrate one methodology in which an electrical stimulus may stimulate an electroactive polymer inner member to radially expand and radially collapse, thereby providing a pumping action designed to assist the heart in circulating blood within the body. For example, FIG. 7 illustrates the example medical device 10 described with respect to FIG. 6 positioned within an example body lumen 30. The medical device 10 may include an inner member 18 (e.g., inner sleeve) positioned within a stent member 11, a first valve 40 and a second valve 41. Further, FIG. 7 illustrates that the medial portion 34 of the inner member 18 may extend radially inward of the inner surface 32 of the stent 11. Therefore, it can be appreciated that the medial portion 34 of the inner member 18 may be able to flex radially inward and radially outward relative to the longitudinal axis 50 of the medical device 10.

As discussed above, the inner member 18 of the medical device 10 may be formed from an electroactive polymer material. It can be appreciated that the electroactive polymer material may be able the change shape in response to an electrical stimulus provided thereto. For example, FIG. 7 illustrates that as an electrical stimulus is applied via the conductive member 20 to the individual electrodes of the electrode sets 42a-42d, the inner member 18 may expand radially outward (relative to the longitudinal axis 50). Further, it can be appreciated that the expansion of the inner member 18 radially outward may create an area of low pressure within the inner member 18, thereby allowing blood to be drawn into the lumen of the inner member 18 through the valve 41 of the medical device 10. It can further be appreciated from FIG. 3 that the second end region 14 may correspond to that portion of the medical device 10 closest to the left ventricle of the heart.

The arrow 56 of FIG. 7 represents blood being drawn through the valve 41 and into the lumen of the inner member 18 as it expands radially outward. It is noted that the valve member 40 may remain closed as the inner member 18 expands, thereby preventing blood adjacent to the first end region 12 from being drawn from a region outside the medical device 10 into the lumen of the inner member 18. In other words, the placement of the valve 40 along the first end region 12 may prevent blood from backflowing from the ascending aorta into the lumen of the inner member 18.

FIG. 8 illustrates that when the electrical stimulus is removed, the inner member 18 contracts radially inward relative to the longitudinal axis 50. The contraction may result in an area of high pressure to build within the lumen of the inner member 18. The high pressure may force blood through the valve 40 and into a portion of the blood vessel 30 adjacent the first end region 12 of the medical device 10. It can be appreciated from FIG. 3 that the first end region 12 may correspond to that portion of the medical device 10 closest to the aorta. The arrow 58 of FIG. 8 represents blood being pushed into the aorta as the inner member 18 contracts radially inward. FIG. 7 shows the valve member 40 opening and the valve 41 closing as the inner member 18 contracts to pump blood out of the medical device 10.

Additionally, it can be appreciated that if an electrical stimulus is repetitively delivered to the electroactive material of the inner member 18, the inner member 18 may cycle through the process of expanding to draw blood into the medical device 10 and contracting to push blood out of the medical device 10. In other words, repeated application of the electrical stimulus may allow the medical device 10 to pump blood from the left ventricle into the circulatory system of the body.

Figure 9:
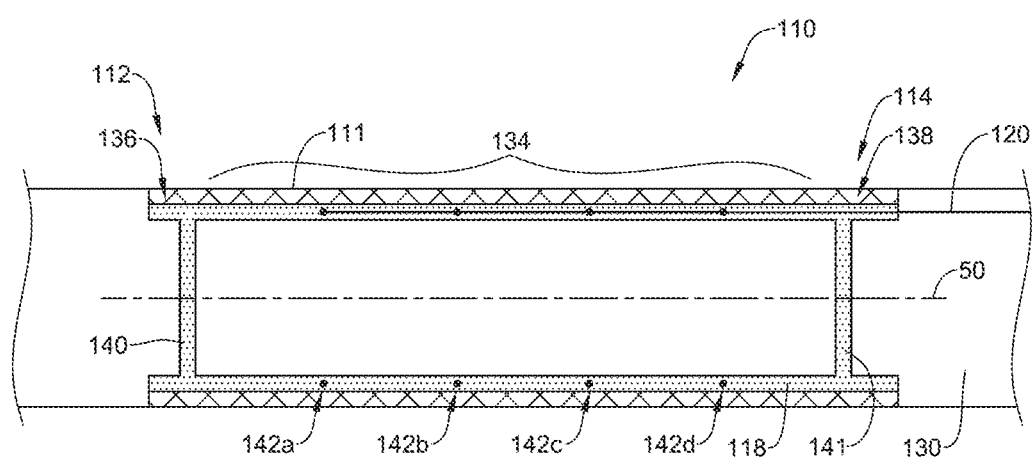
FIG. 9 illustrates another example medical device positioned in a body lumen.

FIG. 9 illustrates another example medical device 110 positioned within a body lumen 130 (e.g., the aorta). The medical device 110 may be similar in form and function to the medical device 10 described above. For example, the medical device 110 may include an inner member 118 positioned within a lumen of a stent member 111. The stent member 111 may include a first end region 112 and a second end region 114. Further, the inner member 118 may be attached to the stent member 111 at a first attachment region 136 and a second attachment region 138. Similarly to that described above with respect to medical device 10, the inner member 118 of medical device 110 may be free from attachment to the inner surface of the stent 111 along the medial region 134. Additionally, FIG. 9 illustrates that the medical device 110 may include a valve 140 (similar to the valve 40 described above) and a valve 141 (similar to the valve 41) disposed along the second end region 114 of the inner member 118.

Further, FIG. 9 illustrates four sets of activation elements (e.g., electrodes) 142a-142d disposed along the inner member 118. As shown in FIG. 9, each of the electrode sets 142a-142d may be spaced apart from one another along the inner member 118. Similarly, to the electrode sets described with respect to medical device 10, each of the electrodes in each electrode set 142a-142d may be located at the same axial position with one another along the longitudinal axis. Further, a conduction member 120 may connect the electrodes defining each of the electrode sets 142a-142d with one another.

As discussed above, the medical device 110 may be utilized to assist the heart in pumping blood through the circulatory system of the body. It can be appreciated that in order for the medical device 110 to sufficiently perform a pumping action, one or more components of the medical device 110 may need to radially contract and squeeze blood out of the medical device 110 and into the circulatory system of the body.

Figure 10:
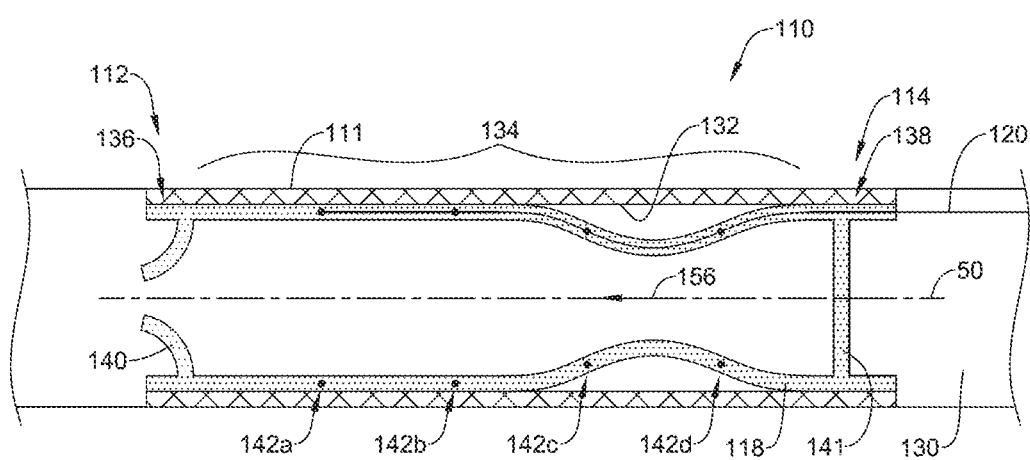
FIG. 10 illustrates the example medical device of FIG. 9 positioned in a body lumen.
Figure 11:
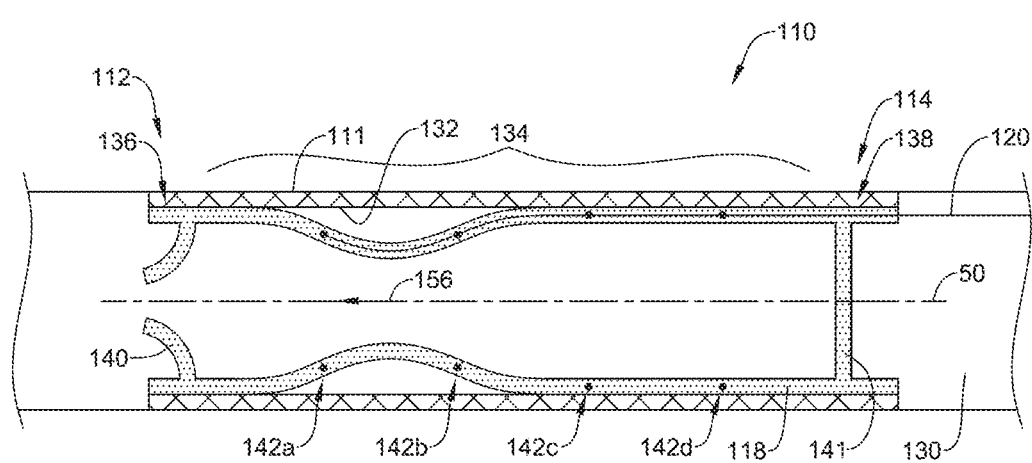
FIG. 11 illustrates the example medical device of FIG. 9 positioned in a body lumen.

FIGS. 10-11 illustrate another example in which an electrical stimulus may stimulate an electroactive polymer inner member to radially expand and radially contract, thereby providing a pumping action designed to assist the heart in circulating blood within the body. However, FIGS. 10-11 illustrate an example in which the inner member is stimulated such that it creates a wave-like motion along the medial portion 134 of the stent 111. The wave-like motion of the inner member 118 may create a pressure differential within the medical device 110 which translates into fluid flow (e.g., pumping) of blood from the heart and into the circulatory system of the body.

For example, FIG. 10 illustrates the example medical device 110 positioned within an example body lumen 130. The medical device 110 may include an inner member 118 (e.g., inner sleeve) positioned within a stent member 111. Further, as illustrated in FIG. 10 illustrates that the medial portion 134 of the inner member 118 may be unattached to the inner surface 132 of the stent 111, and therefore, it can be appreciated that the medial portion 134 of the inner member 118 may be able to flex radially inward and radially outward relative to the longitudinal axis 50 of the medical device 110.

Similar to that discussed above with respect to medical device 110, the inner member 118 of the medical device 110 may be formed from an electroactive polymer material. It can be appreciated that the electroactive polymer material may be able the change shape in response to an electrical stimulus provided thereto. For example, FIG. 10 illustrates that as an electrical stimulus is applied via the conductive member 120 to the individual electrodes of the electrode sets 142c and 142d, the inner member 118 may contract radially inward (relative to the longitudinal axis 50) in an area adjacent to the electrode sets 142c and 142d. It is noted that in FIG. 10 (which illustrates the beginning of the pressure wave described above) the electrical stimulus is not being applied to the electrode sets 142a and 142b, and therefore, the inner member 118 adjacent to the electrode sets 142a and 142b does not, initially, contract radially inward. It can be appreciated that the contraction of the inner member 118 adjacent to the electrode sets 142c and 142d radially inward may push blood through the valve 141 in a direction depicted by the arrow 156.

FIG. 11 illustrates the removal of the electrical stimulus from the electrode sets 142c and 142d and the application of an electrical stimulus to the electrode sets 142a and 142b. As described above, it can be appreciated that that when the electrical stimulus is removed from the electrode sets 142c and 142d, the inner member 118 may relax and expand radially outward toward the inner surface of the stent 111. Further, it can be appreciated that as the electrical stimulus is applied via the conductive member 120 to the individual electrodes of the electrode sets 142a and 142b, the inner member 118 may contract radially inward (relative to the longitudinal axis 50) in an area adjacent to the electrode sets 142a and 142b. It can be appreciated that the medical device 110 may be designed such that the electrical stimulus may advance across the sets of electrodes 142a-142d in series, thereby stimulating each of the sets of electrodes 142a-142d sequentially (the order being set 142d to 142a). As discussed above, the second end region 114 may correspond to that portion of the medical device 10 closest to the left ventricle. It is noted that the valve member 141 may remain closed (while the valve 140 remains open) as the inner member 118 flexes inward and outward, thereby preventing blood from being directed back into the left ventricle of the heart.

Additionally, it can be appreciated that if an electrical stimulus is repeatedly delivered to the electroactive material of the inner member 118, the electrode sets 142a-142d disposed along the inner member 118 may cycle through the process of expanding and contracting to create sequential wave-like contraction which pushes blood in the direction depicted by the arrow 156 in FIG. 10. This wave-like pressure may allow the medical device 10 to pump blood from the left ventricle into the circulatory system of the body. Further, it can be appreciated that as blood is forced in the direction depicted by the arrow 156, the area behind the wave may include an area of low pressure as the wave moves in the direction depicted by the arrow 156. This area of low pressure may "suck in" blood from outside the medical device 10. This inflow may cause the valve 141 to open and let in new blood. The mechanism will repeat, thereby creating flow.

Figure 12:
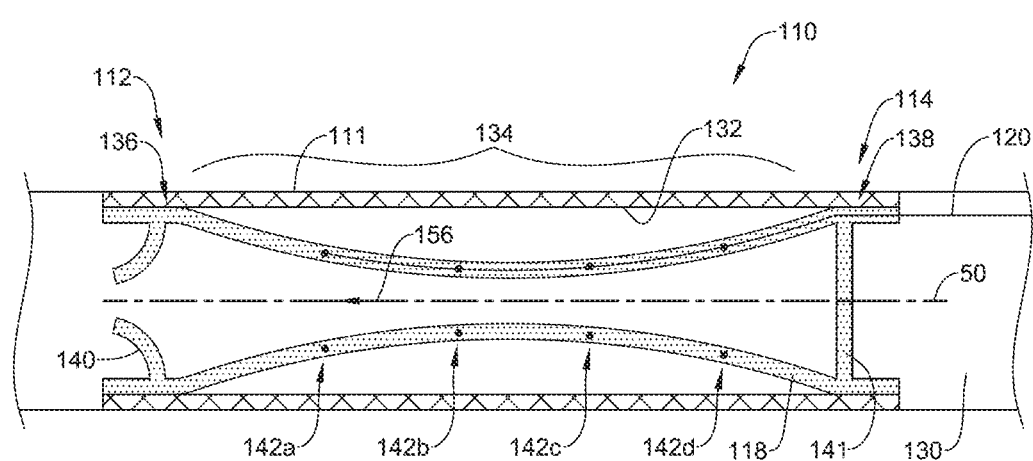
FIG. 12 illustrates another example medical device positioned in a body lumen.

FIG. 12 illustrates another example of how the medical device 110 (described above with respect to FIG. 9) may radially expand and radially contract in response to an electrical stimulus, whereby the repeated expansion and constriction causes a pumping action designed to assist the heart in circulating blood within the body. In particular, FIG. 12 illustrates that the electrode sets 142a-142d of the medical device 110 may be activated in a parallel, whereby the electroactive polymer adjacent to each of the sets of electrodes 142a-142d may be stimulated at the same time, resulting in the contraction of the inner member 118 in a manner illustrated in FIG. 12.

As shown in FIG. 12, the degree of stimulation provided by the electrical stimulus may vary among one or more of the electrode sets 142a-142d. For example, the stimulus delivered to the electrode sets 142b and 142c may be greater than the stimulus delivered to the electrode sets 142a and 142d. It can be appreciated that the larger stimulus may result in the portion of the inner member 118 adjacent to electrode sets 142b and 142c compressing radially inward a greater distance than the portion of the inner member 118 adjacent to the electrode sets 142a and 142d.

In some instances, the contraction of the inner member 118 radially inward (toward the longitudinal axis 50) may cause a region of higher pressure along the medial portion 134 of the medical device 110. The higher pressure may cause blood to be forced out of the medical device 110 (via the valve 140) in a direction shown by the arrow 156. Further, removal of the electrical stimulus may result in the inner member relaxing to a position in which the inner member is adjacent to the inner surface 132 of the stent 111 (e.g., a position described and illustrated with respect to FIG. 9). Additionally, as the inner member 118 expands and returns to a position adjacent the inner surface 132 of the stent 111, a region of low pressure is formed along the medial portion 134 of the medical device 110. The low pressure may cause blood to be drawn into the medical device 110 in a direction opposite to the arrow 156 shown in FIG. 12. It is noted that the valve member 141 may remain closed as the inner member 118 flexes inward and outward, thereby preventing blood from being directed back into the left ventricle of the heart.

Additionally, it can be appreciated that if an electrical stimulus is repeatedly delivered to the electro-active material of the inner member 118, the electrode sets 142a-142d disposed along the inner member 118 may cycle through the process of expanding and contracting to create blood flow through the medical device 110, thereby allowing the medical device 110 to pump blood from the left ventricle into the circulatory system of the body.

Figure 13:
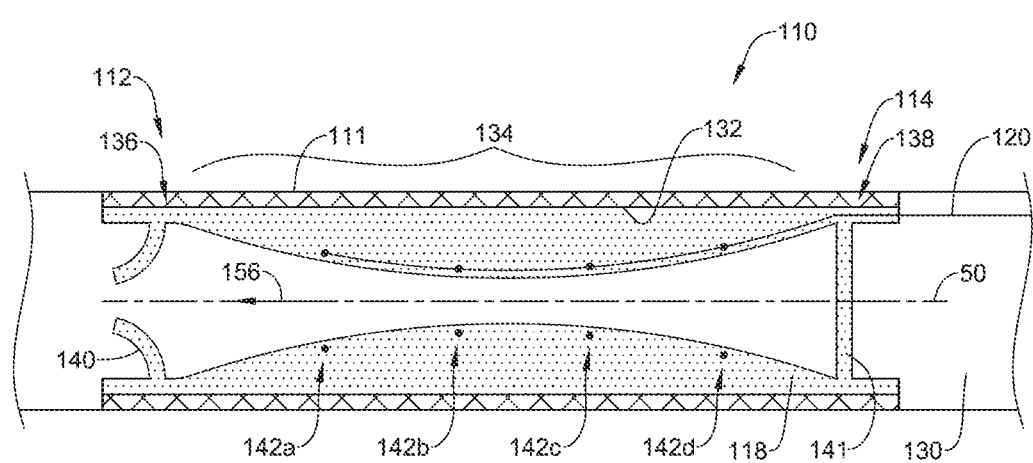
FIG. 13 illustrates another example medical device positioned in a body lumen.

FIG. 13 illustrates another example of how the medical device 110 (described above with respect to FIG. 9) may radially expand and radially contract in response to an electrical stimulus, whereby the repeated expansion and contraction causes a pumping action designed to assist the heart in circulating blood within the body. In particular, FIG. 13 illustrates that as the electrode sets 142a-142d of the medical device 110 are activated in a parallel, the electroactive polymer adjacent to each of the sets of electrodes 142a-142d may be stimulated such that the inner member 118 expands radially inward. It is noted that the inner member 118 shown in FIG. 13 may remain in contact with the inner surface 132 of the stent 111, whereby the wall thickness of the inner member 118 expands radially inward as illustrated in the configuration shown in FIG. 13.

As shown in FIG. 13, the degree of stimulation provided by the electrical stimulus may vary among one or more of the electrode sets 142a-142d. For example, the stimulus delivered to the electrode sets 142b and 142c may be greater than the stimulus delivered to the electrode sets 142a and 142d. It can be appreciated that the larger stimulus may result in the portion of the inner member 118 adjacent to electrode sets 142b and 142c expanding radially inward a greater distance than the portion of the inner member 118 adjacent to the electrode sets 142a and 142d. However, this is not intended to be limiting. Rather, the inner member 118 may expand in a variety of configurations.

In some instances, the expansion of the inner member 118 radially inward (toward the longitudinal axis 50) may cause a region of higher pressure along the medial portion 134 of the medical device 110. The higher pressure may cause blood to be forced out of the medical device 110 (via the valve 140) in a direction shown by the arrow 156. Further, removal of the electrical stimulus may result in the inner member relaxing to a position in which the inner member is adjacent to the inner surface 132 of the stent 111 (e.g., a position described and illustrated with respect to FIG. 9). Additionally, as the inner member 118 relaxes and returns to a position adjacent the inner surface 132 of the stent 111, a region of low pressure is formed along the medial portion 134 of the medical device 110. The low pressure may cause blood to be drawn into the medical device 110 in a direction opposite to the arrow 156 shown in FIG. 12. It is noted that the valve member 141 may remain closed as the inner member 118 expand inward and retracts outward, thereby preventing blood from being directed back into the left ventricle of the heart.

Additionally, it can be appreciated that if an electrical stimulus is repeatedly delivered to the electro-active material of the inner member 118, the electrode sets 142a-142d disposed along the inner member 118 may cycle through the process of expanding and contracting to create blood flow through the medical device 110, thereby allowing the medical device 110 to pump blood from the left ventricle into the circulatory system of the body.

It is contemplated that the pumping mechanism illustrated in FIG. 13 may be utilized in any of the examples disclosed herein. In other words, in any of the examples disclosed herein, the inner member may remain attached to the inner surface of a stent member, whereby the volume of inner member (e.g., the electroactive polymer) increases as the electroactive polymer is stimulated. The volumetric expansion and relaxation of the inner member radially inward (e.g., the increased wall thickness of the inner member) and radially outward may create the pumping action of the medical device as described above.

Figure 14:
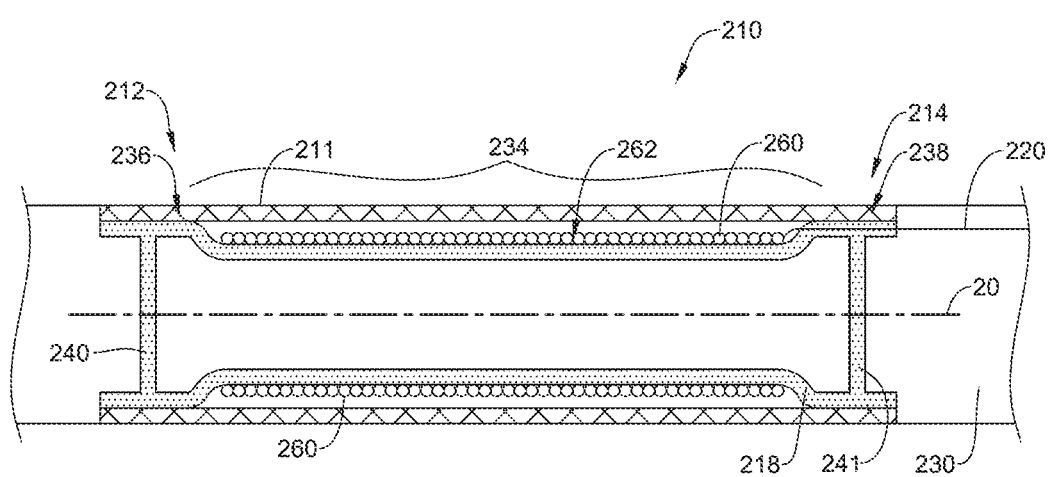
FIG. 14 illustrates another example medical device positioned in a body lumen.

FIG. 14 illustrates another example medical device 210. The medical device 210 may be similar in form and function to the medical device 110 described above. For example, the medical device 210 may include a first end region 212, a second end region 214 and a medial region 234 positioned therebetween. Further, the medical device 210 may include an inner member 218 positioned within a stent member 211. The inner member 218 may be attached to the stent member 211 at a first attachment region 236 and a second attachment region 238. Additionally, the medical device 210 may include a valve 240 (the valve 240 may be similar in form and function to other valve members described above) and/or a valve 241 (the valve 241 may be similar in form and function to other valve members described above).

Additionally, FIG. 14 illustrates that the medical device 210 may include a plurality of activation elements 260 which are positioned along the outer surface 262 of the inner member 218. In some instances, the activation elements may include a plurality of individual artificial muscle strands wrapped around the outer surface 262 of the inner member 218. It can be appreciated that the plurality of artificial muscle strands may be positioned (e.g., aligned) with one another along the outer surface 262 of the inner member 218. Further, FIG. 14 illustrates that the plurality of muscle strands 260 may be coupled to a conductive member 220. It can be appreciated that the conductive member 220 may extend along all the individual muscle strands, whereby the conductive member 220 may be coupled to each of the muscle strands 260 individually. Alternatively, the conductive member 220 may be coupled to a single muscle strand 260 adjacent the second end region 214, whereby each of the subsequent muscle strands 260 are coupled with one another.

Figure 15:
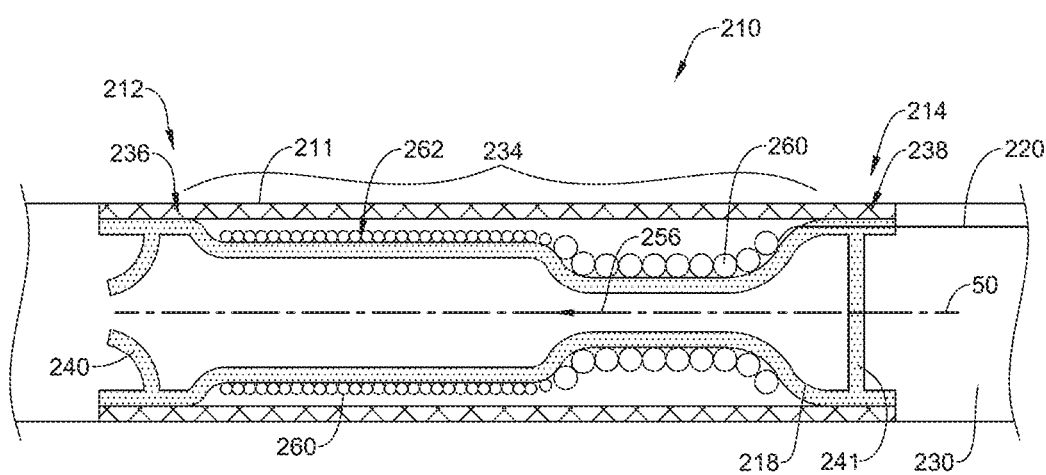
FIG. 15 illustrates the example medical device of FIG. 14 positioned in a body lumen.
Figure 16:
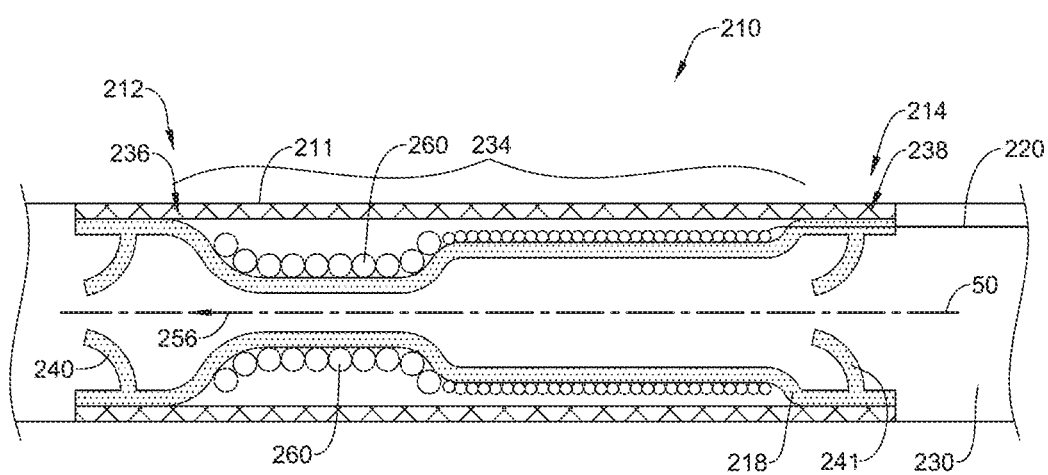
FIG. 16 illustrates the example medical device of FIG. 14 positioned in a body lumen.

FIGS. 15-16 illustrate another example in which an electrical stimulus (provided via the conductive member 220) may stimulate the muscle strands 260 to radially contract the inner member 218, thereby providing a pumping force designed to assist the heart in circulating blood within the body.

For example, FIG. 15 illustrates that as an electrical stimulus is provided to a portion of the muscle strands 260 positioned adjacent to the second end region 214, the muscle strands may contract a portion of the inner member 218 toward the longitudinal axis 50. Similar to the methodology described with respect to FIG. 12, this contraction may cause a region of high pressure which causes blood to flow out of the medical device 210 through the valve 240 in a direction shown by the arrow 256. Additionally, FIGS. 15-16 illustrate that as an electrical stimulus is provided to a one or more of the muscle strands 260, the muscle strands 260 may increase in size. For example, FIGS. 15-16 illustrate an increase in the outer diameter of one or more of the muscle strands 260.

FIG. 16 illustrates the removal of the electrical stimulus from the muscle strands adjacent to the second end region 214 and the application of the electrical stimulus to the muscle strands adjacent to the first end region 212. It can be appreciated that that when the electrical stimulus is removed from muscle strands adjacent to the second end region 214, the inner member 218 may relax and expand radially outward toward the inner surface of the stent 211. As the inner member 218 relaxes and expands radially outward, an area of low pressure may be created adjacent to the portion of the inner member which has expanded radially outward. As illustrated in FIG. 16, this area of low pressure may draw blood into the medical device 210 through the valve 241. It is noted that the valve 241 may be designed as a one-way valve which permits blood to be drawn into the medical device 210 from the left ventricle, while preventing blood from passing back through the valve (and into the left ventricle) when the portion of the inner member 218 adjacent to the second end region 214 is being contracted radially inward (as shown in FIG. 15).

Further, it can be appreciated that as the electrical stimulus is applied via the conductive member 220 to the muscle strands adjacent to the first end region 214, the inner member 218 may contract radially inward (relative to the longitudinal axis 50) in an area adjacent to the second end region 214. It can be appreciated that the medical device 210 may be designed such that the electrical stimulus may advance across the muscles strands 260 in series, thereby stimulating each of the muscle strands in a substantially linear fashion. However, this is not intended to be limiting. It can be appreciated that the muscle strands 260 may be activated in a variety of configurations.

Additionally, it can be appreciated that if an electrical stimulus is repeatedly delivered to the muscle strands 260 positioned along the inner member 218, the muscle strands 260 disposed along the inner member 218 may cycle through the process of expanding and contracting to create a wave-like contraction which pushes blood in the direction depicted by the arrow 256 in FIGS. 15-16. It can be further appreciated that the valve 240 and/or the valve 241 may open and close in response to the wave-like contraction. This wave-like pressure may allow the medical device 210 to pump blood from the left ventricle into the circulatory system of the body.

The materials that can be used for the various components of the medical device 10 (and variations, systems or components thereof disclosed herein) and the various elements thereof disclosed herein may include those commonly associated with medical devices. For simplicity purposes, the following discussion makes reference to the occlusive implant 10 (and variations, systems or components disclosed herein). However, this is not intended to limit the devices and methods described herein, as the discussion may be applied to other elements, members, components, or devices disclosed herein.

In some embodiments, the medical device 10 (and variations, systems or components thereof disclosed herein) may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HAS-TELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the medical device 10 (and variations, systems or components thereof disclosed herein) may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the occlusive implant 10 (and variations, systems or components thereof disclosed herein). Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device 10 (and variations, systems or components thereof disclosed herein) to achieve the same result.

In some embodiments, a degree of Magnetic Resonance Imaging (MRI) compatibility is imparted into the medical device 10 (and variations, systems or components thereof disclosed herein). For example, the medical device 10 (and variations, systems or components thereof disclosed herein) and/or components or portions thereof, may be made of a material that does not substantially distort the image and create substantial artifacts (e.g., gaps in the image). Certain ferromagnetic materials, for example, may not be suitable because they may create artifacts in an MRI image. The medical device 10 (and variations, systems or components disclosed herein) or portions thereof, may also be made from a material that the MRI machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the medical device 10 (and variations, systems or components thereof disclosed herein) and/or portions thereof, may be made from or include a polymer or other suitable material. Some examples of suitable polymers may include copolymers, polyisobutylene-polyurethane, polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments, the sheath can be blended with a liquid crystal polymer (LCP). For example, the mixture can contain up to about 6 percent LCP.

In some embodiments, the medical device 10 (and variations, systems or components thereof disclosed herein) may include a textile material. Some examples of suitable textile materials may include synthetic yarns that may be flat, shaped, twisted, textured, pre-shrunk or un-shrunk. Synthetic biocompatible yarns suitable for use in the present disclosure include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the medical device 10 (and variations, systems or components thereof disclosed herein) may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); anti-neoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vascoactive mechanisms.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A medical device, comprising:
a tubular scaffold, the scaffold including an inner surface and an outer surface;
a flexible inner member extending along at least a portion of the inner surface of the scaffold;
an activation assembly positioned along a portion of the inner member, the activation assembly including a conductive member having a first end region and a second end region, wherein a portion of the first end region is coupled to an activation element, and wherein the second end region is coupled to a power source;
wherein the power source is configured to deliver an electrical stimulus to the activation element, and wherein the electrical stimulus causes the activation element to shift the inner member between a first configuration and a second expanded configuration;
wherein the activation element includes a plurality of electrodes positioned within at least a portion of a wall of the inner member, the plurality of electrodes including a first set of electrodes and a second set of electrodes, wherein each of the first set of electrodes is at the same axial position along a longitudinal axis of the inner member, and wherein the second set of electrodes is spaced away from the first set of electrodes along the longitudinal axis of the inner member.

2. The medical device of claim 1, wherein the inner member includes an electroactive polymer.

3. The medical device of claim 1, wherein each electrode of the first set of electrodes is circumferentially spaced around the longitudinal axis of the inner member.

4. The medical device of claim 1, wherein each of the second set of electrodes is at the same axial position along a longitudinal axis of the inner member.

5. The medical device of claim 1, further comprising a valve, wherein the valve is formed from at least a portion of the inner member.

6. A medical device, comprising:
a tubular scaffold, the scaffold including an inner surface and an outer surface;
a flexible inner member extending along at least a portion of the inner surface of the scaffold;
an activation assembly positioned along a portion of the inner member, the activation assembly including a conductive member having a first end region and a second end region, wherein a portion of the first end region is coupled to an activation element, and wherein the second end region is coupled to a power source;
wherein the power source is configured to deliver an electrical stimulus to the activation element, and wherein the electrical stimulus causes the activation element to shift the inner member between a first configuration and a second expanded configuration:
wherein the inner member includes a first attachment region, a second attachment region and a medial region extending between the first and second attachment regions, and wherein the medial region is free from attachment to the inner surface of the scaffold.

7. The medical device of claim 1, wherein shifting the inner member from the first configuration to the second expanded configuration is configured to draw blood into a lumen of the inner member, and wherein shifting the inner member from the second expanded configuration to the first configuration is configured to pump blood out of the lumen of the inner member.

8. The medical device of claim 1, wherein the activation element includes a plurality of artificial muscle strands positioned along an outer surface of the inner member.

9. The medical device of claim 8, wherein the electrical stimulus causes the artificial muscle strands to shift the inner member between the first configuration and the second expanded configuration.

10. The medical device of claim 9, wherein the electrical stimulus causes the artificial muscle strands to increase the outer diameter of one or more of the muscle strands.

11. A medical stent for pumping blood, comprising:
a tubular scaffold, the scaffold including an inner surface and a lumen extending therein;
a flexible sleeve extending along at least a portion of the inner surface of the scaffold, wherein at least a portion of the sleeve includes an electroactive polymer;
a first valve member;
a second valve member; and
a conductive member having a first end region and a second end region, wherein a portion of the first end region is coupled to the electroactive polymer and wherein the second end region is coupled to a power source;
wherein the power source is configured to deliver an electrical stimulus to the electroactive polymer;
wherein the electrical stimulus causes the electroactive polymer to shift the flexible sleeve between a narrowed configuration and an expanded configuration;
wherein shifting the flexible sleeve from the narrowed configuration to the expanded configuration is configured to draw blood into a lumen of the flexible sleeve via the first valve member, and wherein shifting the flexible sleeve from the expanded configuration to the narrowed configuration is configured to pump blood out of the lumen of the flexible sleeve via the second valve member.

* * * * *